United States Patent [19]

Ivy et al.

[11] Patent Number: 4,670,249

[45] Date of Patent: Jun. 2, 1987

[54] GROWTH-PROMOTING COMPOSITIONS

[75] Inventors: Richard E. Ivy; Glen W. Wolfrom; Bruce D. Burleigh, all of Terre Haute, Ind.

[73] Assignee: International Minerals & Chemical Corp., Terre Haute, Ind.

[21] Appl. No.: 722,408

[22] Filed: Apr. 12, 1985

[51] Int. Cl.⁴ ............... A61K 31/335; A61K 31/365
[52] U.S. Cl. .................................. 424/424; 424/426; 514/9; 514/12; 514/21; 514/450
[58] Field of Search ............ 514/9, 12, 21, 450; 424/22, 19

[56] References Cited

U.S. PATENT DOCUMENTS

| | | | |
|---|---|---|---|
| 2,927,884 | 3/1960 | Segard | 514/12 |
| 3,196,019 | 7/1965 | Andrews et al. | 514/450 |
| 3,239,341 | 3/1966 | Hodge et al. | 514/450 |
| 3,239,345 | 3/1966 | Hodge et al. | 514/450 |
| 3,239,349 | 3/1966 | Hodge et al. | 514/450 |
| 3,887,583 | 6/1975 | Wehrmeister et al. | 549/269 |
| 3,965,274 | 6/1976 | Hidy et al. | 514/450 |
| 4,069,339 | 1/1978 | Ingle et al. | 514/450 |
| 4,192,870 | 3/1980 | Grandadam et al. | 343/408 |
| 4,239,772 | 12/1980 | Shipchandler | 514/450 |
| 4,410,512 | 10/1983 | Bowers | 514/17 |
| 4,414,206 | 11/1983 | Gordon et al. | 514/9 |
| 4,443,470 | 4/1984 | Hodge et al. | 514/450 |
| 4,537,879 | 8/1985 | Hamill et al. | 514/9 |

FOREIGN PATENT DOCUMENTS

| | | |
|---|---|---|
| 103395 | 3/1984 | European Pat. Off. |
| 104920 | 4/1984 | European Pat. Off. |
| 2238476 | 7/1973 | France |

OTHER PUBLICATIONS

Hidy, *Adv. Appl. Microbiol.*, 22:59–82, (1979).

*Primary Examiner*—Ronald W. Griffin
*Attorney, Agent, or Firm*—Thomas L. Farquer; Barbara G. Ernst

[57] ABSTRACT

A composition for promoting the growth or feed conversion efficiency of meat-producing animals which contains growth-promoting amounts of growth hormone and a zearalin.

13 Claims, No Drawings

GROWTH-PROMOTING COMPOSITIONS

BACKGROUND OF THE INVENTION

The present invention relates to novel growth-promoting compositions and methods for their use. More particularly, the invention relates to compositions containing a mixture of anabolic substances.

With the ever-increasing demand for edible protein and the dwindling resources available for producing such protein, there has been considerable interest in developing bioactive substances which can increase the rate of growth or feed conversion efficiency in meat-producing animals. A group of naturally occurring substances that has received considerable attention includes the animal growth hormones.

Growth hormones are polypeptide anabolic hormones secreted by the pituitary glands of many species, including most meat-producing animals. Until fairly recently, growth hormones could be obtained only by extraction from animal tissues. These extraction procedures were arduous, and resulted in small yields of the hormone. With the advent of recombinant DNA technology, it has become possible to clone various animal growth hormone genes and produce the hormones microbially in useful yields at reasonable costs. See European Patent Application 83304574.3 (publication No. 0 103 395) to Biogen N.V.

Endogenous growth hormones stimulate growth, increase the rate of protein synthesis and the mobilization and utilization of fatty acids, and decrease the rate of carbohydrate utilization. Administration of exogenous growth hormones has been shown to increase the rate of growth, weight gain and meat production in animals. Although growth hormones are somewhat species specific, there is considerable homology among the amino acid sequences of animal growth hormones and these hormones have been shown to exhibit inter-species biological activities.

In addition to inter-species activities, various active fragments of growth hormones have been discovered. In particular, it has been found that polypeptides missing several amino acids from the N-terminus maintain a high level of biological activity. The aforementioned European Patent application discloses Δ4 and Δ9 constructions (missing 4 and 9 amino acids from the N-termini respectively) of bovine growth hormone which retain their biological activity. Moreover, biologically active animal growth hormones produced by recombinant DNA techniques often have an extraneous N-terminal methionine.

Another group of anabolic agents which has received a great deal of attention includes the "zearalins." "Zearalins" include zearalenone which is a natural metabolite of the organism *Gibberella zeae* and derivatives thereof. Zearalenone is described by Andrews, F. N., et al., U.S. Pat. No. 3,196,019. A number of active derivatives of zearalenone have been prepared and are described in the patent and technical literature. See Hidy, P. H., et al., *Adv. Appl. Microbiol.* 22, 59–82 (1979). Zearalin are resorcylic acid lactone derivatives. Zearalenone is represented by the following chemical formula:

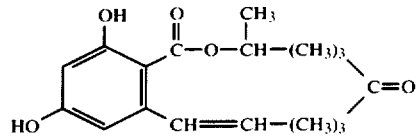

U.S. Pat. No. 3,239,341 describes the reduction of the olefinic bond of zearalenone to produce zearalanone, and U.S. Pat. No. 3,239,345 describes the reduction of both the double bond and the ketone group of zearalenone to produce the compound, zearalanol. The latter compound has enjoyed considerable commercial success as an agent for improving weight gains and feed efficiencies in meat-producing animals. This compound is known by its common name, zeranol, and compositions containing the compound are sold under the trademark, Ralgro ®, by International Minerals and Chemical Corporation, Northbrook, Ill. U.S.A.

SUMMARY OF THE INVENTION

In accordance with the present invention, a composition for promoting the growth or feed efficiency of a meat-producing mammal contains growth-promoting amounts of an animal growth hormone having anabolic activity in said mammal and a zearalin. These compositions have been found to improve both weight gains and feed conversion efficiencies in controlled trials.

DETAILED DESCRIPTION OF THE INVENTION

The zearalin employed in the compositions of the present invention is any of the anabolic compounds represented by the formula

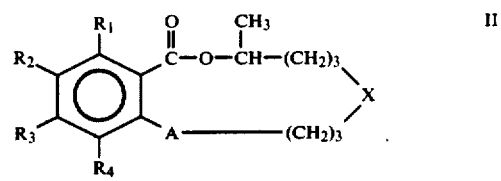

wherein A is $-CH_2CH_2-$ or $-CH=CH-$; X is $-CH_2-$,

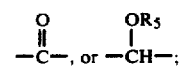

$R_5$ is hydrogen, lower alkyl containing from 1 to about 5 carbon atoms, aryl containing from 6 to about 10 carbon atoms, aralkyl, wherein the aryl portion contains from 6 to about 10 carbon atoms and the alkylene portion contains from 1 to about 5 carbon atoms; or acyl of from 1 to about 5 carbon atoms; $R_1$ and $R_3$ are independently selected from hydrogen, $-OH$, or $OR_6$; $R_6$ is lower alkyl of from 1 to about 5 carbon atoms; and $R_2$ and $R_4$ are independently selected from hydrogen, halogen and $-NO_2$.

The carbon in the lactone ring adjacent the carboxylate group is optically active, and when X is

that group is also optically active. In addition, when A is —CH=CH—, it can be in the cis or trans configuration. All isomers, diastereoisomers and positional isomers are contemplated for use in the compositions of this invention.

In preferred compositions, A is —CH$_2$CH$_2$—, X is

R$_2$ and R$_4$ are hydrogen. The most preferred zearalin is zearalanol which is represented by the above formula, wherein A is —CH$_2$CH$_2$—, R$_2$ and R$_4$ are hydrogen, R$_1$ and R$_3$ are —OH and R$_5$ is hydrogen.

The growth hormones that may be employed in the compositions of this invention may be natural growth hormone extracted from animal pituitary tissue. For economic reasons, the growth hormone preferably is a microbially-produced animal growth hormone made by recombinant DNA techniques. The procedures for making such growth hormones are known, and are described, for example, in the aforementioned European patent application No. 83304574.3 (describing bovine growth hormone) and European patent application No. 83305717.7 (publication No. 0 104 920, describing the production of porcine growth hormone). As used herein, the term growth hormone is intended to include active fragments of the polypeptide hormone as well as the full-length hormone or its fragment having an extraneous N-terminal methionine.

Because of the inter-species biological activities of growth hormones, a composition containing a particular growth hormone may be used in more than one species. For example, compositions containing bovine growth hormone may be administered to cattle, sheep, goats, pigs and other animals to enhance the rate of weight gain and feed conversion efficiency. Any such growth hormone may be employed which exhibits anabolic activity in the species to which the composition is being administered. Preferably, the composition contains growth hormone corresponding to that of the same species to which it is to be administered.

The compositions of this invention are advantageously administered parenterally. Such administration may be by intravenous or intramuscular injection, intraperitoneal injection, or preferably subcutaneous implant. Zearalanol is conventionally administered to animals in the form of a slow-release, subcutaneous implant which is inserted beneath the skin of the ear of the animal. Growth hormones, being polypeptides, cannot conveniently be administered orally, because they are broken down and inactivated in the alimentary tract. Zearalins, on the other hand, can be adminstered orally and thus can be incorporated into animal feeds. Although less preferred, it is contemplated that the method of the present invention could be accomplished by orally administering the zearalin portion of the composition and parenterally administering the growth hormone component.

The growth hormone and zearalin are administered either separately or in combination in growth-promoting amounts. The preferred method is to implant the zearalin in a single dose subcutaneously in the ear (for example, in the case of zeranol, 12 mg for sheep; 36 mg for cattle) and to inject the growth hormone subcutaneously in the form of a long-acting delivery system that will provide small amounts daily to the animal (for example, in the case of bovine growth hormone, 10 mg/day for sheep; 6 mg/day for cattle).

The total dosage of zearalin and growth hormone administered can depend on several factors, including the particular zearalin and growth hormone employed, the delivery systems, and the animal species. The total dosage of zeranol in sheep generally ranges from about 200 to about 600 micrograms per kilogram of body weight, preferably about 300–500 μg/kg and most preferably about 400 μg/kg. The total zeranol dosage in cattle generally ranges from about 50 to about 200 micrograms per kilogram of body weight, preferably about 80–100 μg/kg. In sheep, the total dosage of bovine growth hormone generally ranges from about 100 to about 600 micrograms per kilogram of body weight, preferably about 200–400 μg/kg and most preferably about 300 μg/kg. The total dosage of bovine growth hormone in cattle generally ranges from about 5 to about 40 micrograms per kilogram of body weight, preferably about 12–18 μg/kg.

The preferred dosage form for zearalin is a spherical or cylindrical tablet implanted subcutaneously. Such dosage forms are well known, and are designed such that the active ingredients are slowly released over a period of several days to several weeks. The growth hormone may be incorporated in any of a variety of delivery systems, such as low melting beeswax (*Romansky Formulary*) peanut oil-aluminum monstearate, or a solid semi-permeable implant.

The compositions and methods of the present invention have been found to significantly improve the rate of weight gain and/or feed conversion efficiencies of meat-producing animals. The invention is particularly useful for administration to cattle, sheep, swine, and goats.

The invention is further illustrated by the following examples, which are not intended to be limiting.

EXAMPLE I

Effects of Anabolic Agents on Growing Lambs

The following experiment was conducted to determine the effects of administering bovine growth hormone (bGH), zeranol and combinations of the two on growing lambs. Effects of these agents on weight gain, feed intake, feed/weight gain ratio, blood urea nitrogen (BUN) and blood glucose were measured and recorded.

Sixty-four castrated male spring lambs were involved in the tests. The lambs were of mixed breed and initial weights averaged about 30 kg. Prior to initiating the test procotol, the animals were injected with an anthelminic and vaccinated for contagious ecthyma (soremouth) and *Clostridium perfingens* type D (overeating disease) and were placed on the adaptation schedule shown in Table 1 below.

The protocol involved eight replicates of each of eight treatment regimens (four levels of bGH and two levels of zeranol). Each replicate consisted of a single lamb.

Pituitary-derived bGH was administered daily (at 9:00 a.m.) at levels of 0, 1, 5 and 10 mg per lamb in a single 5 ml subcutaneous injection. The injectable solutions of bGH were prepared by dissolving appropriate amounts of the hormone in "Cornell Buffer," which consisted of isotonic saline containing 0.025 M sodium bicarbonate and 0.025 M sodium carbonate. These solutions were sterilized by filtration and stored at 4° C. until use. Zeranol was administered at 0 and 12 mg per lamb in a single subcutaneous implant three days prior to initiation of the protocol. The zeranol implant used was a commercial product sold by Internatioanl Minerals and Chemical Corp. under the trademark, Ralgro ®. Placebo preparations of the appropriate vehicles comprised the zero levels of bGH and zeranol.

The experiment was continued for 28 days. The lambs were weighed at weekly intervals and initial and final weights were determined by averaging the weights taken on two consecutive days. Throughout the test, lambs were given water and fed ad libitum a ration having the composition shown in Table 2. Feed consumption was recorded. Blood samples were taken biweekly and analyzed for BUN and glucose.

Average daily weight gain (ADG), average daily feed intake (ADF), feed intake to weight gain ratio (F/G), BUN and blood glucose levels were recorded and analyzed statistically. The effects of bGH on ADG, ADF and F/G are shown in Table 3. The effects of zeranol on ADG, ADF and F/G are summarized in Table 4. Interactive effects of bGH and zeranol on ADG, ADF and F/G are summarized in Table 5. These data demonstrate an additive effect of the two anabolic agents, and suggest that the two agents have different modes of action in vivo.

The effects of bGH, zeranol and combinations on BUN and blood glucose levels are summarized in Tables 6, 7 and 8 respectively.

TABLE 1

Pretest Adaptation Schedule

| | kg per head daily | |
|---|---|---|
| Days After Arrival | Alfalfa-corn plant[a] Pellets | Basal[a] Ration |
| 0–12 | 1.4 | 0.0 |
| 13–14 | 1.0 | 0.4 |
| 15–16 | 0.6 | 0.8 |
| 17–18 | 0.2 | 1.2 |
| 19–20 | 0.0 | 1.4 |

[a]See Table 2

TABLE 2

Composition of the Basal Ration

| | International Reference No. | Percent |
|---|---|---|
| Ingredients: | | |
| Corn, cracked sheled | 4-02-931 | 68.7 |
| Alfalfa-whole corn plant, dehy.[a] | | 20.0 |
| Soybean meal (44% protein) | 5-20-637 | 7.5 |
| Cane molasses | 4-04-696 | 2.0 |
| Limestone | 6-02-632 | 0.8 |
| Trace mineral salt[b] | | 0.6 |
| Vitamin premix[c] | | 0.4 |
| Calculated Composition: | | |
| Crude protein | | 11.9 |
| Crude fiber | | 6.8 |
| Calcium | | 0.48 |
| Phosphorous | | 0.28 |
| Potassium | | 0.73 |
| Sulfur | | 0.27 |

TABLE 2-continued

Composition of the Basal Ration

| | International Reference No. | Percent |
|---|---|---|
| Digestible Energy | | 3.08 Mcal/ka |

[a]Charles H. Schenk and Sons, Inc., Vincennes, IN. Guaranteed analysis: crude protein, min. 12.00%; crude fiber, max. 25.00%; fat, min. 1.50%; calcium, min. 0.75%, max. 0.87%; and phosphorous, min. 0.20%.
[b]Composition: NaCl, not >99.0% and not <95.0%; and not <0.35% Zn, 0.34% Fe, 0.200% Mn, 0.033% Cu, >0.077% I, and 0.005% Co.
[c]Provides per kg of diet: 2,750 IU vitamin A; 700 IU vitamin D, and 10 IU vitamin E.

TABLE 3

Effect of bGH on Average Daily Gain (ADG), Average Daily Feed Intake (ADF) and Feed/Gain (F/G) in Lambs

| | bGH, mg/lamb/day | | | | |
|---|---|---|---|---|---|
| Item | 0 | 1 | 5 | 10 | SEM[a] |
| No. Animals | 13 | 10 | 14 | 12 | |
| ADG, Kg | | | | | |
| Week 1 | 0.35 | 0.37 | 0.36 | 0.34 | 0.0329 |
| Week 2[b] | 0.35 | 0.32 | 0.34 | 0.45 | 0.0320 |
| Week 3 | 0.22 | 0.27 | 0.29 | 0.28 | 0.0351 |
| Week 4[c] | 0.17 | 0.29 | 0.31 | 0.33 | 0.0237 |
| Final[d] | 0.27 | 0.29 | 0.31 | 0.33 | 0.0142 |
| ADF, Kg | | | | | |
| Week 1 | 1.42 | 1.27 | 1.29 | 1.28 | 0.0603 |
| Week 2 | 1.35 | 1.28 | 1.31 | 1.42 | 0.0480 |
| Week 3[e] | 1.34 | 1.30 | 1.24 | 1.38 | 0.0535 |
| Week 4 | 1.30 | 1.32 | 1.25 | 1.27 | 0.0472 |
| Final | 1.36 | 1.28 | 1.28 | 1.34 | 0.0412 |
| F/G | | | | | |
| Week 1 | 4.30 | 3.83 | 3.88 | 3.86 | 0.268 |
| Week 2[b] | 3.74 | 3.84 | 3.72 | 3.33 | 0.310 |
| Week 3 | 5.51 | 5.73 | 4.76 | 6.03 | 0.733 |
| Week 4[d] | 5.89 | 5.57 | 6.72 | 4.22 | 0.567 |
| Final[d] | 4.81 | 4.59 | 4.27 | 4.10 | 0.201 |

[a]SEM = Standard error of the mean.
[b]GH had a linear (P < .05) effect.
[c]GH had a linear (P < .10) effect.
[d]GH had a linear (P < .01) effect.
[e]GH had a quadratic (P = .056) effect.

TABLE 4

Effect of Zeranol on ADG, ADF, and F/G in Lambs

| Item | 0 mg | 12 mg | SEM[a] |
|---|---|---|---|
| No. Animals | 25 | 24 | |
| ADG, Kg | | | |
| Week 1 | 0.34 | 0.36 | 0.0232 |
| Week 2[b] | 0.32 | 0.41 | 0.0226 |
| Week 3 | 0.25 | 0.28 | 0.0248 |
| Week 4 | 0.22 | 0.23 | 0.0167 |
| Final[b] | 0.28 | 0.32 | 0.0101 |
| ADF, Kg | | | |
| Week 1 | 1.36 | 1.28 | 0.0425 |
| Week 2 | 1.35 | 1.33 | 0.0339 |
| Week 3 | 1.29 | 1.33 | 0.0377 |
| Week 4 | 1.29 | 1.28 | 0.0333 |
| Final | 1.31 | 1.32 | 0.0290 |
| F/G | | | |
| Week 1[c] | 4.30 | 3.69 | 0.189 |
| Week 2 | 3.74 | 3.93 | 0.219 |
| Week 3 | 5.51 | 5.85 | 0.517 |
| Week 4 | 5.89 | 5.54 | 0.400 |
| Final[d] | 4.81 | 4.19 | 0.147 |

[a]SEM = Standard error of the mean.
[b]Zeranol had an effect (P < .01)
[c]Zeranol had an effect (P < .05).

TABLE 5

Effect of bGH on Average Daily Gain (ADG), Feed Intake (ADF), and Feed/Gain (F/G) in Lambs Implanted with 0 or 12 mg bGH

| | Zeranol, mg/head | | | | | | | | |
|---|---|---|---|---|---|---|---|---|---|
| | 0 mg bGH, mg/day | | | | 12 mg bGH, mg/day | | | | |
| Item | 0 | 1 | 5 | 10 | 0 | 1 | 5 | 10 | SEM[a] |
| No. Animals | 7 | 5 | 7 | 6 | 6 | 5 | 7 | 6 | |
| ADG, Kg | | | | | | | | | |
| Week 1 | 0.30 | 0.34 | 0.34 | 0.36 | 0.37 | 0.39 | 0.38 | 0.31 | 0.0464 |
| Week 2 | 0.31 | 0.35 | 0.24 | 0.38 | 0.39 | 0.29 | 0.44 | 0.51 | 0.0452 |
| Week 3 | 0.19 | 0.27 | 0.27 | 0.28 | 0.25 | 0.28 | 0.31 | 0.29 | 0.0496 |
| Week 4 | 0.17 | 0.25 | 0.20 | 0.28 | 0.18 | 0.25 | 0.26 | 0.24 | 0.0334 |
| Final | 0.25 | 0.28 | 0.26 | 0.33 | 0.30 | 0.30 | 0.34 | 0.33 | 0.0201 |
| ADF, Kg | | | | | | | | | |
| Week 1 | 1.41 | 1.23 | 1.31 | 1.45 | 1.43 | 1.31 | 1.27 | 1.11 | 0.0852 |
| Week 2 | 1.34 | 1.22 | 1.42 | 1.40 | 1.37 | 1.34 | 1.20 | 1.44 | 0.0678 |
| Week 3 | 1.34 | 1.27 | 1.52 | 1.40 | 1.33 | 1.32 | 1.32 | 1.36 | 0.0755 |
| Week 4 | 1.31 | 1.32 | 1.22 | 1.32 | 1.29 | 1.31 | 1.28 | 1.22 | 0.0667 |
| Final | 1.34 | 1.26 | 1.23 | 1.41 | 1.38 | 1.30 | 1.33 | 1.26 | 0.0581 |
| F/G | | | | | | | | | |
| Week 1 | 4.73 | 4.08 | 1.25 | 4.05 | 4.02 | 3.58 | 3.51 | 3.67 | 0.378 |
| Week 2 | 4.40 | 3.87 | 3.22 | 3.45 | 4.41 | 3.81 | 4.21 | 3.22 | 0.438 |
| Week 3 | 6.63 | 3.74 | 4.51 | 6.02 | 5.91 | 6.72 | 5.01 | 6.05 | 1.035 |
| Week 4 | 6.38 | 5.68 | 7.23 | 3.92 | 5.85 | 5.46 | 6.20 | 4.52 | 0.800 |
| Final | 5.47 | 4.73 | 4.71 | 4.34 | 4.68 | 4.37 | 3.89 | 3.86 | 0.284 |

TABLE 6

Effect of bGH on Blood Glucose and Blood Urea Nitrogen (BUN)

| | bGH, mg/day | | | | |
|---|---|---|---|---|---|
| Item | 0 | 1 | 5 | 10 | SEM[a] |
| No. Animals | 14 | 12 | 14 | 15 | |
| Glucose, mg/dl | | | | | |
| 14 days (L.001)[b] | 82.8 | 80.5 | 86.7 | 96.4 | 2.24454 |
| 28 days | 77.3 | 71.0 | 73.9 | 77.0 | 2.70770 |
| BUN, mg/dl | | | | | |
| 14 days (L.001) | 9.7 | 11.6 | 7.0 | 5.0 | 0.64093 |
| 28 days (L.001) | 15.5 | 15.0 | 11.9 | 8.5 | 0.73756 |

[a]SEM = Standard error of the means
[b]L.001 = Significant linear effects of bGH (P < .001)

TABLE 7

Effect of Zearanol on Blood Glucose and Blood Urea Nitrogen (BUN)

| Item | 0 mg | 12 mg | SEM[a] |
|---|---|---|---|
| No. Animals | 28 | 27 | |
| Glucose, mg/dl | | | |
| 14 days | 87.9 | 86.0 | 1.59238 |
| 28 days | 74.0 | 76.0 | 1.92095 |
| BUN, mg/dl | | | |
| 14 days[b] | 8.8 | 7.5 | 0.45470 |
| 28 days | 13.0 | 12.1 | 0.52326 |

[a]SEM = Standard error of the means
[b]Means are signfiicantly different (P < .03).

TABLE 8

Effect of bGH and Zaranol on Blood Glucose and Blood Urea Nitrogen (BUN)

| | 0 mg Zearanol bGH, mg/day | | | | 12 mg Zearanol bGH, mg/day | | | | |
|---|---|---|---|---|---|---|---|---|---|
| Item | 0 | 1 | 5 | 10 | 0 | 1 | 5 | 10 | SEM[a] |
| No. Animals | 7 | 6 | 7 | 8 | 7 | 6 | 7 | 7 | |
| Glucose, mg/dl | | | | | | | | | |
| 14 days | 82.4 | 82.0 | 86.9 | 98.0 | 83.1 | 78.9 | 86.5 | 94.6 | 3.18596 |
| 28 days | 79.6 | 71.3 | 90.4 | 74.1 | 75.0 | 70.7 | 77.3 | 80.3 | 3.84336 |
| BUN, mg/dl | | | | | | | | | |
| 14 days[b] | 9.3 | 12.5 | 8.9 | 5.3 | 10.1 | 10.6 | 5.0 | 4.6 | 0.90975 |
| 28 days | 15.6 | 15.1 | 13.2 | 9.0 | 15.4 | 15.0 | 10.6 | 7.8 | 1.04691 |

[a]SEM = Standard error of means.
[b]Significant interaction between seranol and bGH (P < .08).

EXAMPLE II

Effect of Anabolic Agents on Growing Cattle

This experiment was done to determine the effect of administering bovine growth hormone (bGH), zeranol, and combinations of the two on growing cattle. Effects of these compounds on blood urea nitrogen (BUN), feed intake (pounds feed per pound of weight gain), and weight gain were recorded.

Materials and Methods

Animals. Steers were received into pens (3 animals/pen) and placed on a three week adaptation schedule. Within one week after receipt, the steers were weighed, tagged, and injected with an authelminic.

Compounds Tested. Pituitary-derived bGH (Parlow) was administered daily at levels of 0, 6, 12 and 24 per steer in a single 20-ml subcutaneous injection. Zeranol (RALGRO ®), at levels of 0 and 36 mg per steer given as a single subcutaenous dose (implant) three days prior to initiation of the study. Placebo preparations of the appropriate vehicles were used at the zero level of bGH and zeranol respectively.

Injectable solutions of bGH were prepared using "Cornell buffer" which consists of isotonic saline containing 0.025M $NaHCO_3$ and 0.025M $Na_2CO_3$. Solutions of bGH were prepared every four days and kept at 4° C. until used. The saline/buffer vehicle was prepared in bulk and sterilized by filtration. bGH added aseptically to the vehicle.

Procedures

The study consisted of a three week adaptation period, a two week pre-test period, and a six week experimental (treatment) period.

During pre-test each animal received daily subcutaneous injections of 20 ml Cornell buffer in the neck region. Upon completion of the pre-test period, sixty-four of the steers were randomly assigned to one of eight treatments (8 animals/treatment group). The remaining 8 animals were randomly assigned among two control groups, if they were within the normal, animal population. During the treatment period (42 days) the animals were injected daily with 0, 6, 12 and 24 mg/hd bGH subcutaneously in 20 ml of Cornell buffer. Three days prior to beginning the experimental period, tereatments 5 through 8 animals were implanted with 36 mg of zeranol. Blood samples (20 to 30 ml) were taken from each steer at the end of th acclimation period, just prior to zeranol implantation during the pre-test period, and at 14 days days, 28 days and 42 days during the treatments period. Samples were taken prior to the daily injection. Serum prepared and analyzed for urea nitrogen, glucose, insulin and growth hormone.

All steers were weighed (unshrunk) weekly during the pre-test and experimental periods. Feed and water were provided ad libitum. Feed was weighed daily. Feed not eaten was weighed back and fresh feed added each day.

Approximately 10 animals were selected at the end of the test from treatments 1 and 4 for both visual and chemical carcass evaluation.

Ration Composition:

| Item | Percent |
|---|---|
| Corn | 66.9 |
| Soybean meal (44%) | 4.5 |
| Alafalfa/corn plant | 25.0 |
| Molasses, cane | 2.5 |
| Trace mineral salt | 0.5 |
| Dicalcium phosphate | 0.4 |
| Limestone | 0.1 |
| Vitamin ADE premix | 0.1 |
| | 100.0 |

Calculated Composition (as-fed basis)

| | |
|---|---|
| Crude protein | 10.9 |
| Crude fiber | 8.5 |
| Crude fat | 2.1 |
| Calcium | 0.36 |
| Phosphorus | 0.32 |

-continued

| | |
|---|---|
| TDN | 72.0 |

Experimental design and Statistics. The experiment was conducted as a 4×2 factorial arrangement of treatments (four levels of bGH and two levels of zeranol) with eight replicates per treatment combination. Each replicate consisted of a single steer. The data was statistically analyzed by a two-way analysis of variance (Sokal and Rohlf, *Biometry*, W. H. Freeman and Co., San Francisco, 1969; pp. 332-323). The form of the response to bGH level (linear, quadratic or cubic) was characterized by the use of orthogonal contrasts, and in the presence of a significant quadratic response, the optimum level was estimated (Gill, J. L. *Design and Analysis of Exprimentals in the Animal and Medical Sciences*, Vol. 1, The Iowa State University Press, Ames, 1978; pp. 168-173).

The following table shows the schedule of treatment numbers with bGH in mg per head per day and zeranol implanted at a single dosage of 36 mg.

TABLE 9

| Zeranol Level | bGH Level | | | |
|---|---|---|---|---|
| | 0 | 6 | 12 | 24 |
| 0 | 1* | 2* | 3* | 4* |
| 36 mg | 5* | 6* | 7* | 8* |

*Denotes Treatment Number

TABLE 10

| Zeranol Level | bGH Mg/HD/Day | | | | |
|---|---|---|---|---|---|
| | 0 | 6 | 12 | 24 | Average |
| 0 | 10.71 | 9.98 | 9.37 | 8.48 | 9.64 |
| 36 mg | 10.71 | 9.71 | 8.10 | 7.88 | 9.10 |
| Average | 10.71 | 9.85 | 8.74 | 8.18 | |

Statistical analysis of the data in Table 10 shown that; in combinations, 5.6% of the improvement in reducing BUN comes from zeranol and 16.7% from bGH.

TABLE 11

Test for Synergism in the BUN Reduction for Combinations of Zeranol and bGH

| Zeranol Level | bGH Mg/HD/Day | | | |
|---|---|---|---|---|
| | 0 | 6 | 12 | 24 |
| 0 | 10.71 | 9.98 | 9.37 | 8.48 |
| 36 mg | 10.71 | 9.71 | 8.10 | 7.88 |
| % Reduction for Combination | | 9.1% | 24.4% | 26.4% |
| % Reduction for Additivity | | 6.3% | 12.5% | 19.2% |

TABLE 12

42-Day Feed Efficiency, Pounds Feed per Pound of Gain

| Zeranol Level | bGH Mg/HD/Day | | | | |
|---|---|---|---|---|---|
| | 0 | 6 | 12 | 24 | Average |
| 0 | 10.0 | 8.6 | 7.3 | 8.2 | 8.6 |
| 36 mg | 8.1 | 7.7 | 7.4 | 7.4 | 7.6 |
| Average | 9.0 | 8.2 | 7.8 | 7.8 | |

The foregoing data show that by using a combination of zeranol and bGH, it is possible to achieve very good improvements in feed efficiencies while lowering the dosage of bGH from 12 to 6 mg/head/day.

TABLE 13

| Zeranol Level | Total Weight Gain for 42-Day Period (Kg) bGH Mg/HD/Day | | | | |
|---|---|---|---|---|---|
| | 0 | 6 | 12 | 24 | Average |
| 0 | 79.2 | 99.8 | 112.7 | 107.6 | 99.1 |
| 36 mg | 100.8 | 112.7 | 113.8 | 107.9 | 108.6 |
| Average | 90.0 | 105.8 | 113.3 | 107.74 | |

The data in Table 13 show that by using a combination of zeranol and bGH, very good weight gains can be achieved even while lowering the dosage of bGH from 12 to 6 mg/head/day.

We claim

1. A composition for promoting the growth or feed efficiency of a meat-producing mammal which comprises growth-promoting amounts of an animal growth hormone having anabolic activity and a zearalin of the formula

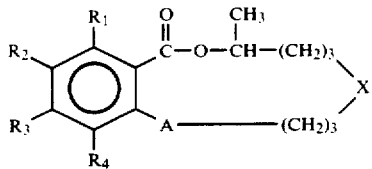

wherein A is —CH$_2$CH$_2$— or —CH=CH—; X is —CH$_2$—,

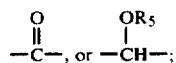

$R_5$ is hydrogen, lower alkyl containing from 1 to about 5 carbon atoms, aryl containing from 6 to about 10 carbon atoms, aralkyl, wherein the aryl portion contains from 6 to about 10 carbon atoms and the alkylene portion contains from 1 to about 5 carbon atoms; or acyl of from 1 to about 5 carbon atoms; $R_1$ and $R_3$ are independently selected from hydrogen, —OH, or OR$_6$; $R_6$ is lower alkyl of from 1 to about 5 carbon atoms; and $R_2$ and $R_4$ are independently selected from hydrogen, halogen and —NO$_2$.

2. The composition of claim 1 for promoting growth or feed efficiency of sheep, which is in the form of a subcutaneous implant containing from about 100 to about 600 micrograms of growth hormone per kg. of animal weight and from about 200 to about 600 micrograms of zearalin per kg. of animal body weight.

3. The composition of claim 1, for promoting growth or feed efficiency of cattle which is in the form of a subcutaneous implant containing from about 5 to about 40 micrograms of growth hormone per kg. of animal body weight and from about 50 to about 200 micrograms of zearalin per kg. of animal body weight.

4. The composition of claim 2, wherein the zearalin is zeranol and the growth hormone is bovine growth hormone, and the implant contains from about 200 to about 400 micrograms of bovine growth hormone per kg. of animal body weight and from about 300 to about 500 micrograms of zeranol per kg of animal body weight.

5. The composition of claim 3, wherein the zearalin is zeranol and the growth hormone is bovine growth hormone, and the implant contains from about 12 to 18 micrograms of bovine growth hormone per kg. of animal body weight and from about 80 to about 100 micrograms of zearalin per kg. of animal body weight.

6. A method for increasing the rate of growth or feed efficiency of a meat-producing mammal, which comprises administering to said mammal growth-promoting amounts of an animal growth hormone having anabolic activity in said mammal and a zearalin of the formula

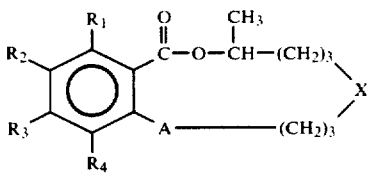

wherein A is —CH$_2$CH$_2$— or —CH=CH—; X is —CH$_2$—,

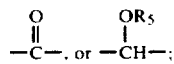

$R_5$ is hydrogen, lower alkyl containing from 1 to about 5 carbon atoms, aryl containing from 6 to about 10 carbon atoms, aralkyl, wherein the aryl portion contains from 6 to about 10 carbon atoms and the alkylene portion contains from 1 to about 5 carbon atoms; or acyl of from 1 to about 5 carbon atoms; $R_1$ and $R_3$ are independently selected from hydrogen, —OH, or OR$_6$; $R_6$ is lower alkyl of from 1 to about 5 carbon atoms; and $R_2$ and $R_4$ are independently selected from hydrogen, halogen and —NO$_2$.

7. The method of claim 6, wherein said mammal is selected from cattle, sheep, pigs and goats.

8. The method of claim 7, wherein said mammal is a sheep, the growth hormone is administered at a dosage of from about 100 to about 600 micrograms per kg. of animal body weight and the zearalin is administered at a dosage of from about 200 to about 600 micrograms per kg. of animal body weight.

9. The method of claim 7, wherein said mammal is bovine, the growth hormone is administered at a dosage of from about 5 to about 40 micrograms per kg. of animal body weight and the zearalin is administered at a dosage of from about 50 to about 200 mcirograms per kg. of animal body weight.

10. The method of claim 8, wherein the zearalin is zearalanol, administered at a dosage of from about 300 to about 500 micrograms per kg. of animal body weight, and the growth hormone is bovine growth hormone, administered at a dosage of from about 200 to about 400 micrograms per kg. of animal weight.

11. The method of claim 9, wherein the zearalin is zearalanol, administered at a dosage of from about 80 to about 100 micrograms per kg of animal body weight, and the growth hormone is bovine growth hormone, administered at a dosage of from about 12 to about 18 micrograms per kg. of animal body weight.

12. The method of claim 6, wherein said growth hormone and zearalin are administered parenterally.

13. The method of claim 6, wherein said zearalin is administered in the form of a subcutaneous implant.

* * * * *

UNITED STATES PATENT AND TRADEMARK OFFICE
CERTIFICATE OF CORRECTION

PATENT NO. : 4,670,249

DATED : June 2, 1987

INVENTOR(S) : Richard E. Ivy et al.

It is certified that error appears in the above-identified patent and that said Letters Patent are hereby corrected as shown below:

Column 4, line 28, "monstearate" should read -- monostearate --

Column 4, line 51, "anthelminic" should read -- anthelmintic --

Column 8, Table 8, in the Heading, "Zaranol" should read -- Zeranol --

Column 8, Table 8, Footnote b, "seranol" should read -- zeranol --

Column 8, line 68, "authelminic" should read -- anthelmintic --

Column 9, lines 32 and 33, "tereatments" should read -- treatments --

Column 9, line 35, "th" should read -- the --

Column 9, line 37, delete the word "days" second occurrence

Column 9, lines 37 and 38, "treatments" should read -- treatment --

Column 10, line 12, "332-323" should read -- 322-323 --

Column 10, line 17, "Exprimentals" should read -- Experiments --

Column 10, line 41, "shown" should read -- shows --

Signed and Sealed this

Twenty-eighth Day of June, 1988

Attest:

DONALD J. QUIGG

Attesting Officer

Commissioner of Patents and Trademarks